(12) United States Patent
Dietz et al.

(10) Patent No.: US 7,910,614 B2
(45) Date of Patent: Mar. 22, 2011

(54) AZOLYLMETHYLOXIRANES, USE THEREOF FOR CONTROLLING PLANT PATHOGENIC FUNGI, AND AGENTS CONTAINING THE SAME

(75) Inventors: Jochen Dietz, Mannheim (DE); Thomas Grote, Wachenheim (DE); Bernd Müller, Frankenthal (DE); Jan Klaas Lohmann, Ludwigshafen (DE); Jens Renner, Bad Dürkheim (DE); Sarah Ulmschneider, Bad Dürkheim (DE); Alice Glättli, Mannheim (DE)

(73) Assignee: BASF SE, Ludwigshafen (DE)

( * ) Notice: Subject to any disclaimer, the term of this patent is extended or adjusted under 35 U.S.C. 154(b) by 121 days.

(21) Appl. No.: 12/374,877

(22) PCT Filed: Jul. 17, 2007

(86) PCT No.: PCT/EP2007/057353
§ 371 (c)(1),
(2), (4) Date: Jan. 23, 2009

(87) PCT Pub. No.: WO2008/012234
PCT Pub. Date: Jan. 31, 2008

(65) Prior Publication Data
US 2009/0325801 A1  Dec. 31, 2009

(30) Foreign Application Priority Data
Jul. 25, 2006 (EP) .................................. 06117788

(51) Int. Cl.
*A61K 31/4196* (2006.01)
*C07D 405/14* (2006.01)
(52) U.S. Cl. .................... 514/383; 548/266.2; 548/266.6
(58) Field of Classification Search ........................ None
See application file for complete search history.

(56) References Cited

U.S. PATENT DOCUMENTS

| | | | |
|---|---|---|---|
| 4,061,656 A | 12/1977 | Klaus et al. | |
| 4,116,975 A | 9/1978 | Klaus et al. | |
| 4,464,381 A | 8/1984 | Janssen et al. | |
| 4,652,580 A | 3/1987 | Janssen et al. | |
| 4,723,042 A | 2/1988 | Janssen et al. | |
| 4,804,785 A | 2/1989 | Janssen et al. | |
| 4,906,652 A | 3/1990 | Karbach et al. | |
| 4,914,128 A | 4/1990 | Schirmer et al. | |
| 4,935,245 A | 6/1990 | Horn et al. | |
| 5,118,511 A | 6/1992 | Horn et al. | |
| 5,162,357 A | 11/1992 | Seele et al. | |
| 6,211,387 B1 | 4/2001 | Napoletano et al. | |
| 6,277,791 B1 | 8/2001 | Assmann et al. | |
| 6,313,147 B1 | 11/2001 | Shaber et al. | |
| 6,372,692 B1 | 4/2002 | Assmann et al. | |
| 6,448,228 B1 | 9/2002 | Filippini et al. | |
| 6,642,181 B2 | 11/2003 | Assmann et al. | |
| 6,812,229 B1 | 11/2004 | Ozaki et al. | |
| 6,875,783 B2 | 4/2005 | Assmann et al. | |
| 7,098,227 B2 | 8/2006 | Dunkel et al. | |
| 7,157,481 B2 | 1/2007 | Assmann et al. | |
| 2006/0178374 A1 | 8/2006 | Cui et al. | |
| 2007/0232670 A1 | 10/2007 | Assmann et al. | |
| 2009/0197929 A1 | 8/2009 | Dietz et al. | |
| 2009/0203700 A1 | 8/2009 | Dietz et al. | |
| 2009/0270256 A1 | 10/2009 | Dietz et al. | |
| 2009/0305887 A1 | 12/2009 | Dietz et al. | |
| 2010/0087321 A1 | 4/2010 | Renner et al. | |
| 2010/0167924 A1 | 7/2010 | Dietz et al. | |
| 2010/0179058 A1 | 7/2010 | Dietz et al. | |

FOREIGN PATENT DOCUMENTS

| | | |
|---|---|---|
| CA | 2 011 087 | 9/1990 |
| CA | 2 012 596 | 9/1990 |
| CA | 2 048 974 | 3/1992 |
| CA | 2287470 | 10/1998 |
| DE | 2 651 968 | 5/1977 |
| DE | 3 601 927 | 7/1987 |
| DE | 39 42 333 | 6/1991 |
| EP | 0 094 564 | 11/1983 |
| EP | 0 174 769 | 3/1986 |
| EP | 0 196 038 | 10/1986 |

(Continued)

OTHER PUBLICATIONS

International Search Report for International Application No. PCT/EP2007/057353; International Filing Date: Jul. 17, 2007.

(Continued)

*Primary Examiner* — Yong Chu
*Assistant Examiner* — Michael Barker
(74) *Attorney, Agent, or Firm* — Brinks Hofer Gilson & Lione

(57) ABSTRACT

The present invention relates to azolylmethyloxiranes of the general formula I

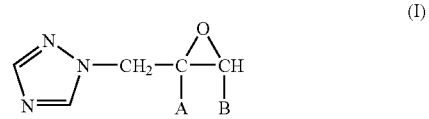

in which
A or B is benzodioxolyl which is optionally substituted by one to five of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio,
and the respective other substituent
A or B is phenyl or 5-membered or 6-membered heteroaryl, these substituents optionally being substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio,
and to the plant-compatible acid addition salts or metal salts thereof, to the use of the compounds of the formula I for controlling phytopathogenic fungi and to compositions comprising these compounds.

16 Claims, No Drawings

FOREIGN PATENT DOCUMENTS

| | | |
|---|---|---|
| EP | 226 917 | 7/1987 |
| EP | 0 386 557 | 9/1990 |
| EP | 0 388 871 | 9/1990 |
| EP | 0 421 125 | 4/1991 |
| EP | 0 474 045 | 3/1992 |
| EP | 10 28 125 | 8/2000 |
| EP | 10 35 122 | 9/2000 |
| EP | 12 01 648 | 5/2002 |
| WO | WO 92/05145 | 4/1992 |
| WO | WO 98/46608 | 10/1998 |
| WO | WO 99/24413 | 5/1999 |
| WO | WO 99/29645 | 6/1999 |
| WO | WO 03/014103 | 2/2003 |
| WO | WO 03/053145 | 7/2003 |
| WO | WO 03/066609 | 8/2003 |
| WO | WO 2004/049804 | 6/2004 |
| WO | WO 2006/021886 | 3/2006 |
| WO | WO 2007/147769 | 12/2007 |
| WO | WO 2007/147778 | 12/2007 |
| WO | WO 2007/147841 | 12/2007 |
| WO | WO 2008/003607 | 1/2008 |
| WO | WO 2008/003622 | 1/2008 |
| WO | WO 2008/012246 | 1/2008 |
| WO | WO 2008/077724 | 7/2008 |

OTHER PUBLICATIONS

International Preliminary Report on Patentability for International Application No. PCT/EP2007/057353; International Filing Date: Jul. 17, 2007.

English Translation of the International Preliminary Report on Patentability for International Application No. PCT/EP2007/057353; International Filing Date: Jul. 17, 2007.

Banwell et al., "Utilization of 1-aryl-2,2-dibromocyclopropanes in synthetic approaches to phenanthroquinolizidine and phenanthroindolizidine alkaloids", Australian Journal of Chemistry, 57(6), 537-548 (2004).

Bazzini, Cristina, et al., "Synthesis and Characterization of Some Aza[5]helicenes", Eur. J. Org. Chem, 2005, 1247-1257.

Clinch et al., "Synthesis of substituted tetrahydropyridines and m-hydroxybenzoic acids", Tetrahedron, 45(1), 239-258 (1989).

Creary, Xavier, "Reaction of organometallic reagents with ethyl trifluoroacetate and diethyl oxalate. Formation of trifluoromethyl ketones and α-keto esters via stable tetrahedral adducts", Journal of Organic Chemistry, 52(22), 5026-5030 (1987).

Epple, R. et al., "3,4,5-Trisubstituted isoxazoles as novel PPARδ agonists. Part 2", Bioorganic & Medicinal Chemistry Letters, 16, 5488-5492 (2006).

Evans, Owen R., et al., "Rational Design of Nonlinear Optical Materials Based on 2D Coordination Networks", Chem. Matter, 2001, p. 3009-3017, vol. 13.

Grushin, V. et al., "Transformations of chloroarenes, catalyzed by transition-metal complexes", Chem. Rev. 94, 1047-1062 (1994).

Hadfield et al., "Synthesis and evaluation of double bond substituted combretastatins", European Journal of Medicinal Chemistry, 40(6), 529-541 (2005).

Hameka, Hendrik, F., "Computation of the Structures of the Phenyl and Benzyl Radicals with the UHF Method", J. Org. Chem., 1987, p. 5025-5026, vol. 52.

Hammer et al., "Stereoselective Synthesis of thiophenedimethyl- and benzenedimethyl-α,α'-bridged bis(glycines)", Acta Chemica Scandinavica, 51(3), 392-402 (1997).

Heuser et al., "Synthesis of novel cyclopropylic sulfones and sulfonamides acting as glucokinase activators", Tetrahedron Letters, 47(16), 2675-2678 (2006).

Klett et al., "Cumulene photochemistry: Photorearrangements of tetraphenyl and triphenyl $C_3$ isomers", Journal of the American Chemical Society, 107(13), 3963-3971 (1985).

Mali et al., "Useful Synthesis of Coumestans", Synthetic Communications, 20(12), 1781-1791 (1990).

Marquis, Annie et al., "Messages in Molecules: Ligand/Cation Coding and Self-Recognition in a Constitutionally Dynamic System of Heterometallic Double Helicates", Chemistry Euro J, 2006, p. 5632-5641, vol. 12.

Ogle et al., "Chiral lithiothiophenes as non-transferable ligands in organocuprate conjugate addition reactions", Tetrahedron: Asymmetry, 14(21), 3281-3283 (2003).

Patani, George, et al., "Bioisosterism: A Rational Approach in Drug Design", Chem. Rev., 1996, p. 3147-3176, vol. 96.

Romines, K. et al., "Structure-activity relationship studies of novel benzophenones leading to the discovery of a potent, next generation HIV nonnucleoside reverse transcriptase inhibitor", J. Med. Chem, 49, 727-739 (2006).

Romo et al., "Diastereoselective cyclopropanations of chiral bicyclic lactams leading to enantiomerically pure cyclopropanes. Application to the total synthesis of CIS-(1S, 3R)-deltamethrinic acid and R-(−)-dictyopterene C'", Tetrahedron, 46(13-14), 4951-4994 (1990).

Shimizu et al., "Effective synthesis of tamoxifen using nickel-catalyzed arylative carboxylation", Synlett, (18), 3182-3184 (2006).

Shizuka, Haruo et al., "Excited-State Proton-Transfer Reactions of Naphthylammonium Ion-18-Crown-6 Complexes", J. Am. Chem. Soc., 1985, p. 3956-3963, vol. 107.

Sundermeier, M. et al., "Progress in the palladium-catalyzed cyanation of aryl chlorides", Chem. Eur. J. 9:8, 1828-1836 (2003).

Tessier et al., "(Z)-Tamoxifen and tetrasubstituted alkenes and dienes via a regio- and stereopsecific three-component magnesium carbometalation palladium (0) cross-coupling strategy", Organic Letters, 5(17), 2989-2992 (2003).

Tsuge, Akihiko, et al., "Self-assembled coordination cage derived from small-sized pyridinophane", Tetrahedron Letters, 2006, p. 6607-6609, vol. 47.

Vu et al., "Stereoselective preparation of functionalized unsaturated lactones and esters via functionalized magnesium carbenoids", Synthesis, (12), 1797-1802 (2003).

Zhang, X. et al., "Synthesis and SAR of novel hydantoin derivatives as selective androgen receptor modulators", Bioorganic & Medicinal Chemistry Letters, 16, 5763-5766 (2006).

Zheng et al., "Design, synthesis, and biological evaluation of the N-diarylalkenyl-piperidinecarboxylic acid derivatives as GABA uptake inhibitors (I)", Bioorganic & Medicinal Chemistry Letters, 16(1), 225-227 (2006).

AZOLYLMETHYLOXIRANES, USE THEREOF FOR CONTROLLING PLANT PATHOGENIC FUNGI, AND AGENTS CONTAINING THE SAME

This application is a National Stage application of International Application No. PCT/EP2007/057353 filed Jul. 17, 2007, the entire contents of which is hereby incorporated herein by reference. This application also claims the benefit under 35 U.S.C. §119 of European Patent Application No. 06117788.7, filed Jul. 25, 2006, the entire contents of which is hereby incorporated herein by reference.

The present invention relates to azolylmethyloxiranes of the general formula I

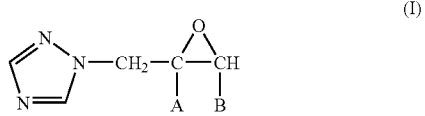

in which
A or B is benzodioxolyl which is optionally substituted by one to five of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio,
and the respective other substituent
A or B is phenyl or 5-membered or 6-membered heteroaryl, these substituents optionally being substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio,
and to the plant-compatible acid addition salts or metal salts thereof.

Furthermore, the invention relates to the use of the compounds of the formula I for controlling phytopathogenic fungi and to compositions comprising these compounds.

Azolylmethyloxiranes, their preparation and their use in crop protection are known, for example, from EP-A 0 094 564 and EP-A 0 196 038.

Azolylmethyloxiranes which carry a hetaryl substituent on the oxirane ring are known from EP-A 0 421 125.

The azolylmethyloxiranes described already have good to very good fungicidal activity against a number of pathogens; however, it was the object of the present invention to provide novel azolylmethyloxiranes having improved fungicidal activity.

This object was achieved with the compounds of the formula I described at the outset.

Owing to the basic character of their nitrogen atoms, the compound I is capable of forming salts or adducts with inorganic or organic acids or with metal ions.

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead and also of the elements of transition groups one to eight, in particular chromium, manganese, iron, cobalt, nickel, copper, zinc, and others. Particular preference is given to the metal ions of the elements of transition groups of the fourth period. The metals can be present in the various valencies that they can assume.

The preparation of the compounds of the formula I is known and described in detail in EP-A 0 094 564, EP-A 0 196 038 and EP-A 0 421 125.

In the definitions of the symbols given in the formulae above, collective terms are used which are generally representative of the substituents below:

Halogen: fluorine, chlorine, bromine and iodine.

Alkyl and the alkyl moieties of composite groups such as, for example, alkylamino: saturated, straight-chain or branched hydrocarbon radicals having preferably 1 to 4 carbon atoms, such as methyl, ethyl, propyl, 1-methylethyl, butyl, 1-methylpropyl, 2-methylpropyl and 1,1-dimethylethyl.

Haloalkyl: alkyl as mentioned above, where some or all of the hydrogen atoms in these groups are replaced by halogen atoms as mentioned above. In one embodiment, the alkyl groups are substituted at least once or completely by a particular halogen atom, preferably fluorine, chlorine or bromine. In a further embodiment, the alkyl groups are partially or fully halogenated by different halogen atoms; in the case of mixed halogen substitutions, the combination of chlorine and fluorine is preferred. Particular preference is given to ($C_1$-$C_4$)-haloalkyl, more preferably ($C_1$-$C_2$)-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

Alkoxy: an alkyl group as defined above which is attached via an oxygen, preferably having 1 to 4 carbon atoms. Examples of preferred alkoxy groups are: methoxy, ethoxy, n-propoxy, 1-methylethoxy, butoxy, 1-methylpropoxy, 2-methylpropoxy or 1,1-dimethylethoxy.

Haloalkoxy: alkoxy as defined above, where some or all of the hydrogen atoms in these groups are replaced by halogen atoms as described above under haloalkyl, in particular fluorine, chlorine or bromine. Examples of preferred haloalkoxy radicals are $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

Alkylthio: alkyl as defined above which is attached via a sulfur atom.

5-membered heteroaryl which contains one, two, three or four nitrogen atoms or one, two or three nitrogen atoms and/or one sulfur or oxygen atom, where the heteroaryl may be attached via carbon or nitrogen, if present: 5-membered heteroaryl groups which, in addition to carbon atoms, may contain one to four nitrogen atoms or one to three nitrogen atoms and/or one sulfur or oxygen atom as ring members, for example furyl, thienyl, pyrrolyl, pyrazolyl, imidazolyl, triazolyl (1,2,3-; 1,2,4-triazolyl), tetrazolyl, oxazolyl, isoxazolyl, 1,3,4-oxadiazolyl, thiazolyl, isothiazolyl and thiadiazolyl, in particular 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl which contains one, two, three or four, preferably one, two or three, nitrogen atoms, where the heteroaryl may be attached via carbon or nitrogen, if present: 6-membered heteroaryl groups which, in addition to carbon atoms, may contain one to four or one to three nitrogen atoms as ring members, for example pyridinyl, pyrimidinyl, pyrazinyl, pyridazinyl, 1,2,3-triazinyl, 1,2,4-triazinyl, 1,3,5-triazinyl, in particular 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The novel compounds of the formula I contain chiral centers and are generally obtained in the form of racemates or as diastereomer mixtures of erythro and threo forms. The erythro and threo diastereomers of the compounds according to the invention can be separated and isolated in pure form, for example, on the basis of their different solubilities or by column chromatography. Using known methods, such uniform pairs of diastereomers can be used to obtain uniform enantiomers. Suitable for use as antimicrobial agents are both the uniform diastereomers or enantiomers and mixtures thereof obtained in the synthesis. This applies correspondingly to the fungicidal compositions.

The compounds according to the invention may be present in various crystal modifications which may differ in their biological activity. They are likewise provided by the present invention.

In the compounds of the formula I according to the invention or in the compounds of the formula I used according to the invention, the following meanings of the substituents, in each case on their own or in combination, are particularly preferred. Here, the preferred substituents or preferred combinations of substituents apply, if appropriate, correspondingly to the precursors of the compounds according to the invention.

The substituent A or B is benzodioxolyl which is optionally substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

According to one embodiment, benzodioxolyl is located in the 3,4-position of the phenyl ring if it denotes substituent A.

According to a further embodiment, benzodioxolyl is located in the 2,3-position of the phenyl ring if it denotes substituent B.

According to a further embodiment, A or B is benzodioxolyl which is substituted by one to three further substituents selected from the group consisting of halogen, $C_1$-$C_4$-alkyl, $C_1$-$C_4$-alkoxy, $C_1$-$C_4$-haloalkyl and $C_1$-$C_4$-haloalkoxy.

According to another embodiment, the substituent A or B is benzodioxolyl which is substituted by one to three further substituents selected from the group consisting of halogen, $C_1$-$C_4$-alkyl and $C_1$-$C_4$-alkoxy.

According to another embodiment, the substituent A or B is benzodioxolyl which is substituted by one to three halogens.

In a preferred embodiment, the substituent A or B is benzodioxolyl which is substituted by one or two further substituents selected from the group consisting of halogen.

In a further preferred embodiment, the substituent A or B is benzodioxolyl which is substituted by two halogen in the dioxolyl ring.

In a further preferred embodiment, the substituent A or B is benzodioxolyl which is substituted by two F in the dioxolyl ring.

In a preferred embodiment, the substituent A or B is benzodioxolyl which is substituted in the dioxolyl ring by two F and in the phenyl ring by a further substituent selected from the group consisting of F, Cl, methyl and methoxy such that the substituents A1, B1 to A18, B18 of the following formulae are obtained:

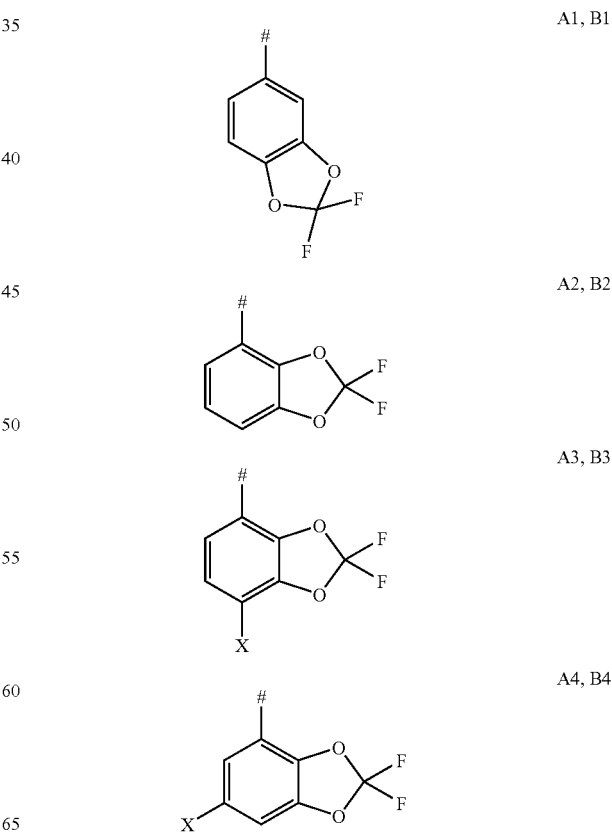

A5, B5
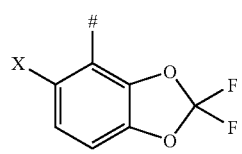
A6, B6
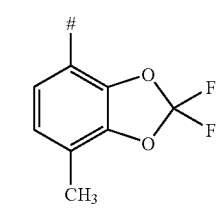
A7, B7
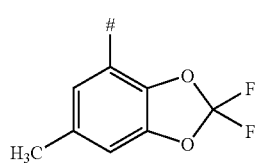
A8, B8
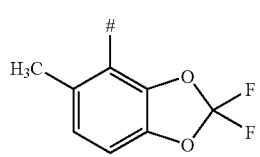
A9, B9
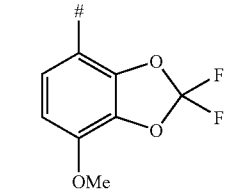
A10, B10
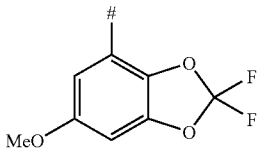
A11, B11
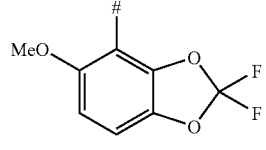
A12, B12
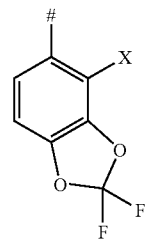
A13, B13
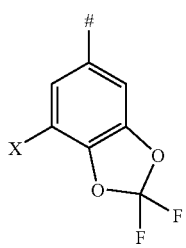
A14, B14
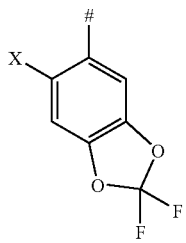
A15, B15
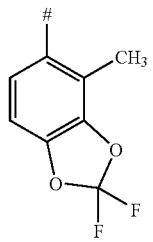
A16, B16
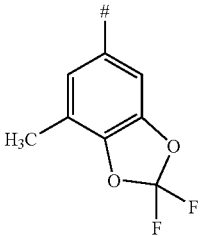
A17, B17
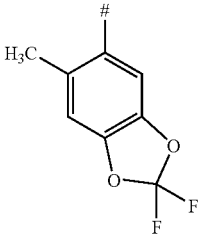
A18, B18
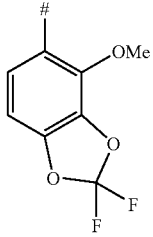

-continued

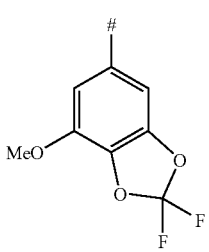
A19, B19

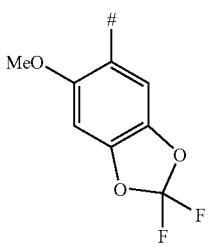
A20, B20

According to one embodiment, A is A1.
According to one embodiment, A is A2.
According to one embodiment, A is A3 where X=F.
According to one embodiment, A is A3 where X=Cl.
According to a further embodiment, A is A4 where X=F.
According to a further embodiment, A is A4 where X=Cl.
According to a further embodiment, A is A5 where X=F.
According to a further embodiment, A is A5 where X=Cl.
According to a further embodiment, A is A6.
According to a further embodiment, A is A7.
According to a further embodiment, A is A8.
According to a further embodiment, A is A9.
According to a further embodiment, A is A10.
According to a further embodiment, A is A11.
According to a further embodiment, A is A12 where X=F.
According to a further embodiment, A is A12 where X=Cl.
According to a further embodiment, A is A13 where X=F.
According to a further embodiment, A is A13 where X=Cl.
According to a preferred embodiment, A is A14 where X=F.
According to a preferred embodiment, A is A14 where X=Cl.
According to a further embodiment, A is A15.
According to a further embodiment, A is A16.
According to a further embodiment, A is A17.
According to a further embodiment, A is A18.
According to a further embodiment, A is A19.
According to a further embodiment, A is A20.
According to one embodiment, B is B1.
According to one embodiment, B is B2.
According to one embodiment, B is B3 where X=F.
According to one embodiment, B is B3 where X=Cl.
According to a further embodiment, B is B4 where X=F.
According to a further embodiment, B is B4 where X=Cl.
According to a further embodiment, B is B5 where X=F.
According to a further embodiment, B is B5 where X=Cl.
According to a further embodiment, B is B6.
According to a further embodiment, B is B7.
According to a further embodiment, B is B8.
According to a further embodiment, B is B9.
According to a further embodiment, B is B10.
According to a further embodiment, B is B11.
According to a further embodiment, B is B12 where X=F.
According to a further embodiment, B is B12 where X=Cl.
According to a further embodiment, B is B13 where X=F.
According to a further embodiment, B is B13 where X=Cl.
According to a preferred embodiment, B is B14 where X=F.
According to a preferred embodiment, B is B14 where X=Cl.
According to a further embodiment, B is B15.
According to a further embodiment, B is B16.
According to a further embodiment, B is B17.
According to a further embodiment, B is B18.
According to a particularly preferred embodiment, B is B19.
According to a further embodiment, B is B20.

In a further embodiment of the present invention, the respective other substituent A or B is phenyl which is substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the respective other substituent A or B is phenyl which is substituted by one to three of the following substituents: halogen, $C_1$-$C_4$-alkyl, $C_1$-$C_4$-alkoxy, $C_1$-$C_4$-haloalkyl or $C_1$-$C_4$-haloalkoxy.

In a preferred embodiment, the respective other substituent A or B is phenyl which is substituted by one to three halogen.

In a further embodiment, the respective other substituent A or B is a 5-membered heteroaryl which is optionally substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the respective other substituent A or B is a 5-membered heteroaryl selected from the group consisting of furyl, thienyl, pyrrolyl, pyrazolyl, imidazolyl, triazolyl, tetrazolyl, oxazolyl, isoxazolyl, 1,3,4-oxadiazolyl, thiazolyl, isothiazolyl and thiadiazolyl.

In a further embodiment, the respective other substituent A or B is a 5-membered heteroaryl selected from the group consisting of furyl, thienyl, pyrrolyl, pyrazolyl, triazolyl and thiazolyl.

In a further embodiment, the respective other substituent A or B is a 5-membered heteroaryl selected from the group consisting of thienyl, triazolyl and pyrazolyl.

In a further embodiment, the respective other substituent A or B is a 5-membered heteroaryl which is substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the respective other substituent A or B is a 5-membered heteroaryl which is substituted by one to three of the following substituents: halogen, $C_1$-$C_4$-alkyl, $C_1$-$C_4$-alkoxy, $C_1$-$C_4$-haloalkyl or $C_1$-$C_4$-haloalkoxy.

In a further embodiment, the respective other substituent A or B is a 5-membered heteroaryl which is substituted by one to three of the following substituents: halogen, $C_1$-$C_4$-alkyl or $C_1$-$C_4$-alkoxy.

In a further embodiment, the respective other substituent A or B is a 6-membered heteroaryl which is optionally substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the respective other substituent A or B is a 6-membered heteroaryl selected from the group consisting of pyridinyl, pyrimidinyl, pyrazinyl, pyridazinyl, 1,2,3-triazinyl, 1,2,4-triazinyl and 1,3,5-triazinyl.

In a further embodiment, the respective other substituent A or B is a 6-membered heteroaryl selected from the group consisting of pyridyl and pyrimidinyl.

In a further embodiment, the respective other substituent A or B is a 6-membered heteroaryl which is substituted by one to three of the following substituents: halogen, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the respective other substituent A or B is a 6-membered heteroaryl which is substituted by one to three of the following substituents: halogen, $C_1$-$C_4$-alkyl, $C_1$-$C_4$-alkoxy, $C_1$-$C_4$-haloalkyl or $C_1$-$C_4$-haloalkoxy.

In a further embodiment, the respective other substituent A or B is a 6-membered heteroaryl which is substituted by one to three of the following substituents: halogen, $C_1$-$C_4$-alkyl or $C_1$-$C_4$-alkoxy.

In particular with a view to their use, preference is given to the compounds I according to the invention compiled in Tables 3 to 54 below. The groups mentioned for a substituent in the tables are furthermore per se, independently of the combination in which they are mentioned, a particularly preferred embodiment of the substituent in question.

TABLE 1

| Row | Substituent B |
|---|---|
| 1-1 | 2-methylphenyl |
| 1-2 | 3-methylphenyl |
| 1-3 | 4-methylphenyl |
| 1-4 | 2-methoxyphenyl |
| 1-5 | 3-methoxyphenyl |
| 1-6 | 4-methoxyphenyl |
| 1-7 | 2-chlorophenyl |
| 1-8 | 3-chlorophenyl |
| 1-9 | 4-chlorophenyl |
| 1-10 | 2-fluorophenyl |
| 1-11 | 3-fluorophenyl |
| 1-12 | 4-fluorophenyl |
| 1-13 | 2-chloro-3-methoxyphenyl |
| 1-14 | 2-chloro-4-methoxyphenyl |
| 1-15 | 2,3-dichlorophenyl |
| 1-16 | 2,4-dichlorophenyl |
| 1-17 | 3,4-dichlorophenyl |
| 1-18 | 2,3-difluorophenyl |
| 1-19 | 2,4-difluorophenyl |
| 1-20 | 2-chloro-3-fluorophenyl |
| 1-21 | 2-chloro-4-fluorophenyl |
| 1-22 | 2-pyridinyl |
| 1-23 | 3-pyridinyl |
| 1-24 | 4-pyridinyl |
| 1-25 | 2-chloropyridin-4-yl |
| 1-26 | 3-chloropyridin-4-yl |
| 1-27 | 2,6-dichloropyridin-4-yl |
| 1-28 | 3,5-dichloropyridin-4-yl |
| 1-29 | 3,6-dichloropyridin-4-yl |
| 1-30 | 2-fluoropyridin-4-yl |
| 1-31 | 3-fluoropyridin-4-yl |
| 1-32 | 2-chloropyridin-3-yl |
| 1-33 | 4-chloropyridin-3-yl |
| 1-34 | 5-chloropyridin-3-yl |
| 1-35 | 6-chloropyridin-3-yl |
| 1-36 | 2,4-dichloropyridin-3-yl |
| 1-37 | 2,5-dichloropyridin-3-yl |
| 1-38 | 2,6-dichloropyridin-3-yl |
| 1-39 | 2-fluoropyridin-3-yl |
| 1-40 | 4-fluoropyridin-3-yl |
| 1-41 | 5-fluoropyridin-3-yl |
| 1-42 | 6-fluoropyridin-3-yl |
| 1-43 | 3-chloropyridin-2-yl |
| 1-44 | 4-chloropyridin-2-yl |
| 1-45 | 5-chloropyridin-2-yl |
| 1-46 | 6-chloropyridin-2-yl |
| 1-47 | 3-fluoropyridin-2-yl |
| 1-48 | 4-fluoropyridin-2-yl |

TABLE 1-continued

| Row | Substituent B |
|---|---|
| 1-49 | 5-fluoropyridin-2-yl |
| 1-50 | 6-fluoropyridin-2-yl |
| 1-51 | 2-methylpyridin-4-yl |
| 1-52 | 3-methylpyridin-4-yl |
| 1-53 | 2-methylpyridin-3-yl |
| 1-54 | 4-methylpyridin-3-yl |
| 1-55 | 5-methylpyridin-3-yl |
| 1-56 | 6-methylpyridin-3-yl |
| 1-57 | 3-methylpyridin-2-yl |
| 1-58 | 4-methylpyridin-2-yl |
| 1-59 | 5-methylpyridin-2-yl |
| 1-60 | 6-methylpyridin-2-yl |
| 1-61 | 2-methoxypyridin-4-yl |
| 1-62 | 3-methoxypyridin-4-yl |
| 1-63 | 2-methoxypyridin-3-yl |
| 1-64 | 4-methoxypyridin-3-yl |
| 1-65 | 5-methoxypyridin-3-yl |
| 1-66 | 6-methoxypyridin-3-yl |
| 1-67 | 3-methoxypyridin-2-yl |
| 1-68 | 4-methoxypyridin-2-yl |
| 1-69 | 5-methoxypyridin-2-yl |
| 1-70 | 6-methoxypyridin-2-yl |
| 1-71 | 6-chloropyrimidin-3-yl |
| 1-72 | 6-methylpyrimidin-3-yl |
| 1-73 | 2-pyrimidinyl |
| 1-74 | 4-pyrimidinyl |
| 1-75 | 5-pyrimidinyl |
| 1-76 | 6-methoxypyrimidin-3-yl |
| 1-77 | 2,4-dichloropyrimidin-3-yl |
| 1-78 | 2,6-dichloropyrimidin-3-yl |
| 1-79 | 2,4-difluoropyrimidin-3-yl |
| 1-80 | 2,6-difluoropyrimidin-3-yl |
| 1-81 | 2-thienyl |
| 1-82 | 3-thienyl |
| 1-83 | 2-chlorothien-3-yl |
| 1-84 | 4-chlorothien-3-yl |
| 1-85 | 5-chlorothien-3-yl |
| 1-86 | 2,5-dichlorothien-3-yl |
| 1-87 | 2,4,5-trichlorothien-3-yl |
| 1-88 | 2-bromothien-3-yl |
| 1-89 | 4-bromothien-3-yl |
| 1-90 | 5-bromothien-3-yl |
| 1-91 | 2,5-dibromothien-3-yl |
| 1-92 | 2,4,5-tribromothien-3-yl |
| 1-93 | 3-pyrazolyl |
| 1-94 | 4-pyrazolyl |
| 1-95 | 1-methylpyrazol-3-yl |
| 1-96 | 1-methylpyrazol-4-yl |
| 1-97 | 1-methylpyrazol-5-yl |
| 1-98 | 2-imidazolyl |
| 1-99 | 4-imidazolyl |
| 1-100 | 1-methylimidazol-2-yl |
| 1-101 | 1-methylimidazol-4-yl |
| 1-102 | 1-methylimidazol-5-yl |
| 1-103 | 1,5-dimethylimidazol-4-yl |
| 1-104 | 1,2-dimethylimidazol-5-yl |
| 1-105 | 1,4-dimethylimidazol-5-yl |

TABLE 2

| Row | Substituent A |
|---|---|
| 2-1 | 2-methylphenyl |
| 2-2 | 3-methylphenyl |
| 2-3 | 4-methylphenyl |
| 2-4 | 2-methoxyphenyl |
| 2-5 | 3-methoxyphenyl |
| 2-6 | 4-methoxyphenyl |
| 2-7 | 2-chlorophenyl |
| 2-8 | 3-chlorophenyl |
| 2-9 | 4-chlorophenyl |
| 2-10 | 2-fluorophenyl |
| 2-11 | 3-fluorophenyl |
| 2-12 | 4-fluorophenyl |
| 2-13 | 2-chloro-3-methoxyphenyl |

TABLE 2-continued

| Row | Substituent A |
|---|---|
| 2-14 | 2-chloro-4-methoxyphenyl |
| 2-15 | 2,3-dichlorophenyl |
| 2-16 | 2,4-dichlorophenyl |
| 2-17 | 3,4-dichlorophenyl |
| 2-18 | 2,3-difluorophenyl |
| 2-19 | 2,4-difluorophenyl |
| 2-20 | 2-chloro-3-fluorophenyl |
| 2-21 | 2-chloro-4-fluorophenyl |
| 2-22 | 2-pyridinyl |
| 2-23 | 3-pyridinyl |
| 2-24 | 4-pyridinyl |
| 2-25 | 2-chloropyridin-4-yl |
| 2-26 | 3-chloropyridin-4-yl |
| 2-27 | 2,6-dichloropyridin-4-yl |
| 2-28 | 3,5-dichloropyridin-4-yl |
| 2-29 | 3,6-dichloropyridin-4-yl |
| 2-30 | 2-fluoropyridin-4-yl |
| 2-31 | 3-fluoropyridin-4-yl |
| 2-32 | 2-chloropyridin-3-yl |
| 2-33 | 4-chloropyridin-3-yl |
| 2-34 | 5-chloropyridin-3-yl |
| 2-35 | 6-chloropyridin-3-yl |
| 2-36 | 2,4-dichloropyridin-3-yl |
| 2-37 | 2,5-dichloropyridin-3-yl |
| 2-38 | 2,6-dichloropyridin-3-yl |
| 2-39 | 2-fluoropyridin-3-yl |
| 2-40 | 4-fluoropyridin-3-yl |
| 2-41 | 5-fluoropyridin-3-yl |
| 2-42 | 6-fluoropyridin-3-yl |
| 2-43 | 3-chloropyridin-2-yl |
| 2-44 | 4-chloropyridin-2-yl |
| 2-45 | 5-chloropyridin-2-yl |
| 2-46 | 6-chloropyridin-2-yl |
| 2-47 | 3-fluoropyridin-2-yl |
| 2-48 | 4-fluoropyridin-2-yl |
| 2-49 | 5-fluoropyridin-2-yl |
| 2-50 | 6-fluoropyridin-2-yl |
| 2-51 | 2-methylpyridin-4-yl |
| 2-52 | 3-methylpyridin-4-yl |
| 2-53 | 2-methylpyridin-3-yl |
| 2-54 | 4-methylpyridin-3-yl |
| 2-55 | 5-methylpyridin-3-yl |
| 2-56 | 6-methylpyridin-3-yl |
| 2-57 | 3-methylpyridin-2-yl |
| 2-58 | 4-methylpyridin-2-yl |
| 2-59 | 5-methylpyridin-2-yl |
| 2-60 | 6-methylpyridin-2-yl |
| 2-61 | 2-methoxypyridin-4-yl |
| 2-62 | 3-methoxypyridin-4-yl |
| 2-63 | 2-methoxypyridin-3-yl |
| 2-64 | 4-methoxypyridin-3-yl |
| 2-65 | 5-methoxypyridin-3-yl |
| 2-66 | 6-methoxypyridin-3-yl |
| 2-67 | 3-methoxypyridin-2-yl |
| 2-68 | 4-methoxypyridin-2-yl |
| 2-69 | 5-methoxypyridin-2-yl |
| 2-70 | 6-methoxypyridin-2-yl |
| 2-71 | 6-chloropyrimidin-3-yl |
| 2-72 | 6-methylpyrimidin-3-yl |
| 2-73 | 2-pyrimidinyl |
| 2-74 | 4-pyrimidinyl |
| 2-75 | 5-pyrimidinyl |
| 2-76 | 6-methoxypyrimidin-3-yl |
| 2-77 | 2,4-dichloropyrimidin-3-yl |
| 2-78 | 2,6-dichloropyrimidin-3-yl |
| 2-79 | 2,4-difluoropyrimidin-3-yl |
| 2-80 | 2,6-difluoropyrimidin-3-yl |
| 2-81 | 2-thienyl |
| 2-82 | 3-thienyl |
| 2-83 | 2-chlorothien-3-yl |
| 2-84 | 4-chlorothien-3-yl |
| 2-85 | 5-chlorothien-3-yl |
| 2-86 | 2,5-dichlorothien-3-yl |
| 2-87 | 2,4,5-trichlorothien-3-yl |
| 2-88 | 2-bromothien-3-yl |
| 2-89 | 4-bromothien-3-yl |
| 2-90 | 5-bromothien-3-yl |
| 2-91 | 2,5-dibromothien-3-yl |
| 2-92 | 2,4,5-tribromothien-3-yl |
| 2-93 | 3-pyrazolyl |
| 2-94 | 4-pyrazolyl |
| 2-95 | 1-methyl-pyrazol-3-yl |
| 2-96 | 1-methyl-pyrazol-4-yl |
| 2-97 | 1-methyl-pyrazol-5-yl |
| 2-98 | 2-imidazolyl |
| 2-99 | 4-imidazolyl |
| 2-100 | 1-methylimidazol-2-yl |
| 2-101 | 1-methylimidazol-4-yl |
| 2-102 | 1-methylimidazol-5-yl |
| 2-103 | 1,5-dimethylimidazol-4-yl |
| 2-104 | 1,2-dimethylimidazol-5-yl |
| 2-105 | 1,4-dimethylimidazol-5-yl |

Table 3
  Compounds of the formula I in which A is A1 and B corresponds in each case to a substituent from a row of Table 1.

Table 4
  Compounds of the formula I in which A is A2 and B corresponds in each case to a substituent from a row of Table 1.

Table 5
  Compounds of the formula I in which A is A3 where X=F and B corresponds in each case to a substituent from a row of Table 1.

Table 6
  Compounds of the formula I in which A is A3 where X=Cl and B corresponds in each case to a substituent from a row of Table 1.

Table 7
  Compounds of the formula I in which A is A4 where X=F and B corresponds in each case to a substituent from a row of Table 1.

Table 8
  Compounds of the formula I in which A is A4 where X=Cl and B corresponds in each case to a substituent from a row of Table 1.

Table 9
  Compounds of the formula I in which A is A5 where X=F and B corresponds in each case to a substituent from a row of Table 1.

Table 10
  Compounds of the formula I in which A is A5 where X=Cl and B corresponds in each case to a substituent from a row of Table 1.

Table 11
  Compounds of the formula I in which A is A6 and B corresponds in each case to a substituent from a row of Table 1.

Table 12
  Compounds of the formula I in which A is A7 and B corresponds in each case to a substituent from a row of Table 1.

Table 13
  Compounds of the formula I in which A is A8 and B corresponds in each case to a substituent from a row of Table 1.

Table 14
  Compounds of the formula I in which A is A9 and B corresponds in each case to a substituent from a row of Table 1.

Table 15
  Compounds of the formula I in which A is A10 and B corresponds in each case to a substituent from a row of Table 1.
Table 16
  Compounds of the formula I in which A is A11 and B corresponds in each case to a substituent from a row of Table 1.
Table 17
  Compounds of the formula I in which A is A12 where X=F and B corresponds in each case to a substituent from a row of Table 1.
Table 18
  Compounds of the formula I in which A is A12 where X=Cl and B corresponds in each case to a substituent from a row of Table 1.
Table 19
  Compounds of the formula I in which A is A13 where X=F and B corresponds in each case to a substituent from a row of Table 1.
Table 20
  Compounds of the formula I in which A is A13 where X=Cl and B corresponds in each case to a substituent from a row of Table 1.
Table 21
  Compounds of the formula I in which A is A14 where X=F and B corresponds in each case to a substituent from a row of Table 1.
Table 22
  Compounds of the formula I in which A is A14 where X=Cl and B corresponds in each case to a substituent from a row of Table 1.
Table 23
  Compounds of the formula I in which A is A15 and B corresponds in each case to a substituent from a row of Table 1.
Table 24
  Compounds of the formula I in which A is A16 and B corresponds in each case to a substituent from a row of Table 1.
Table 25
  Compounds of the formula I in which A is A17 and B corresponds in each case to a substituent from a row of Table 1.
Table 26
  Compounds of the formula I in which A is A18 and B corresponds in each case to a substituent from a row of Table 1.
Table 27
  Compounds of the formula I in which A is A19 and B corresponds in each case to a substituent from a row of Table 1.
Table 28
  Compounds of the formula I in which A is A20 and B corresponds in each case to a substituent from a row of Table 1.
Table 29
  Compounds of the formula I in which B is B1 and A corresponds in each case to a substituent from a row of Table 2.
Table 30
  Compounds of the formula I in which B is B2 and A corresponds in each case to a substituent from a row of Table 2.
Table 31
  Compounds of the formula I in which B is B3 where X=F and A corresponds in each case to a substituent from a row of Table 2.
Table 32
  Compounds of the formula I in which B is B3 where X=Cl and A corresponds in each case to a substituent from a row of Table 2.
Table 33
  Compounds of the formula I in which B is B4 where X=F and A corresponds in each case to a substituent from a row of Table 2.
Table 34
  Compounds of the formula I in which B is B4 where X=Cl and A corresponds in each case to a substituent from a row of Table 2.
Table 35
  Compounds of the formula I in which B is B5 where X=F and A corresponds in each case to a substituent from a row of Table 2.
Table 36
  Compounds of the formula I in which B is B5 where X=Cl and A corresponds in each case to a substituent from a row of Table 2.
Table 37
  Compounds of the formula I in which B is B6 and A corresponds in each case to a substituent from a row of Table 2.
Table 38
  Compounds of the formula I in which B is B7 and A corresponds in each case to a substituent from a row of Table 2.
Table 39
  Compounds of the formula I in which B is B8 and A corresponds in each case to a substituent from a row of Table 2.
Table 40
  Compounds of the formula I in which B is B9 and A corresponds in each case to a substituent from a row of Table 2.
Table 41
  Compounds of the formula I in which B is B10 and A corresponds in each case to a substituent from a row of Table 2.
Table 42
  Compounds of the formula I in which B is B11 and A corresponds in each case to a substituent from a row of Table 2.
Table 43
  Compounds of the formula I in which B is B12 where X=F and A corresponds in each case to a substituent from a row of Table 2.
Table 44
  Compounds of the formula I in which B is B12 where X=Cl and A corresponds in each case to a substituent from a row of Table 2.
Table 45
  Compounds of the formula I in which B is B13 where X=F and A corresponds in each case to a substituent from a row of Table 2.
Table 46
  Compounds of the formula I in which B is B13 where X=Cl and A corresponds in each case to a substituent from a row of Table 2.
Table 47
  Compounds of the formula I in which B is B14 where X=F and A corresponds in each case to a substituent from a row of Table 2.

Table 48
Compounds of the formula I in which B is B14 where X=Cl and A corresponds in each case to a substituent from a row of Table 2.
Table 49
Compounds of the formula I in which B is B15 and A corresponds in each case to a substituent from a row of Table 2.
Table 50
Compounds of the formula I in which B is B16 and A corresponds in each case to a substituent from a row of Table 2.
Table 51
Compounds of the formula I in which B is B17 and A corresponds in each case to a substituent from a row of Table 2.
Table 52
Compounds of the formula I in which B is B18 and A corresponds in each case to a substituent from a row of Table 2.
Table 53
Compounds of the formula I in which B is B19 and A corresponds in each case to a substituent from a row of Table 2.
Table 54
Compounds of the formula I in which B is B20 and A corresponds in each case to a substituent from a row of Table 2.

The compounds I are suitable as fungicides. They are distinguished by an excellent activity against a broad spectrum of phytopathogenic fungi from the class of the Ascomycetes, Deuteromycetes, Oomycetes and Basidiomycetes, in particular from the class of the Oomycetes. Some of them are systemically effective and can be used in crop protection as foliar fungicides, as fungicides for seed dressing and as soil fungicides.

They are particularly important in the control of a multitude of fungi on various crop plants, such as wheat, rye, barley, oats, rice, corn, grass, bananas, cotton, soya, coffee, sugar cane, vines, fruit and ornamental plants, and vegetable plants, such as cucumbers, beans, tomatoes, potatoes and cucurbits, and on the seeds of these plants.

They are especially suitable for controlling the following plant diseases:

*Alternaria* species on vegetables, oilseed rape, sugar beet and fruit and rice, such as, for example, *A. solani* or *A. alternata* on potatoes and tomatoes;
*Aphanomyces* species on sugar beet and vegetables;
*Ascochyta* species on cereals and vegetables;
*Bipolaris* and *Drechslera* species on corn, cereals, rice and lawns, such as, for example, *D. maydis* on corn;
*Blumeria graminis* (powdery mildew) on cereals;
*Botrytis cinerea* (gray mold) on strawberries, vegetables, flowers and grapevines;
*Bremia lactucae* on lettuce;
*Cercospora* species on corn, soybeans, rice and sugar beet;
*Cochliobolus* species on corn, cereals, rice, such as, for example, *Cochliobolus sativus* on cereals, *Cochliobolus miyabeanus* on rice;
*Colletotricum* species on soybeans and cotton;
*Drechslera* species, *Pyrenophora* species on corn, cereals, rice and lawns, such as, for example, *D. teres* on barley or *D. tritici-repentis* on wheat;
Esca on grapevines, caused by *Phaeoacremonium chlamydosporium*, *Ph. Aleophilum* and *Formitipora punctata* (syn. *Phellinus punctatus*);
*Exserohilum* species on corn;
*Erysiphe cichoracearum* and *Sphaerotheca fuliginea* on cucumber plants;
*Fusarium* and *Verticillium* species on various plants, such as, for example, *F. graminearum* or *F. culmorum* on cereals or *F. oxysporum* on a multitude of plants, such as, for example, tomatoes;
*Gaeumanomyces graminis* on cereals;
*Gibberella* species on cereals and rice (for example *Gibberella fujikuroi* on rice);
Grainstaining complex on rice;
*Helminthosporium* species on corn and rice;
*Michrodochium nivale* on cereals;
*Mycosphaerella* species on cereals, bananas and groundnuts, such as, for example, *M. graminicola* on wheat or *M. fijiensis* on bananas;
*Peronospora* species on cabbage and bulbous plants, such as, for example, *P. brassicae* on cabbage or *P. destructor* on onion;
*Phakopsara pachyrhizi* and *Phakopsara meibomiae* on soybeans;
*Phomopsis* species on soybeans and sunflowers;
*Phytophthora infestans* on potatoes and tomatoes;
*Phytophthora* species on various plants, such as, for example, *P. capsici* on bell pepper;
*Plasmopara viticola* on grapevines;
*Podosphaera leucotricha* on apple;
*Pseudocercosporella herpotrichoides* on cereals;
*Pseudoperonospora* on various plants, such as, for example, *P. cubensis* on cucumber or *P. humili* on hops;
*Puccinia* species on various plants, such as, for example, *P. triticina*, *P. striformins*, *P. hordei* or *P. graminis* on cereals or *P. asparagi* on asparagus;
*Pyricularia oryzae*, *Corticium sasakii*, *Sarocladium oryzae*, *S. attenuatum*, *Entyloma oryzae* on rice;
*Pyricularia grisea* on lawns and cereals;
*Pythium* spp. on lawns, rice, corn, cotton, oilseed rape, sunflowers, sugar beet, vegetables and other plants, such as, for example, *P. ultiumum* on various plants, *P. aphanidermatum* on lawns;
*Rhizoctonia* species on cotton, rice, potatoes, lawns, corn, oilseed rape, potatoes, sugar beet, vegetables and on various plants, such as, for example, *R. solani* on beet and various plants;
*Rhynchosporium secalis* on barley, rye and triticale;
*Sclerotinia* species on oilseed rape and sunflowers;
*Septoria tritici* and *Stagonospora nodorum* on wheat;
*Erysiphe* (syn. *Uncinula*) *necator* on grapevines;
*Setospaeria* species on corn and lawns;
*Sphacelotheca reilinia* on corn;
*Thievaliopsis* species on soybeans and cotton;
*Tilletia* species on cereals;
*Ustilago* species on cereals, corn and sugar cane, such as, for example, *U. maydis* on corn;
*Venturia* species (scab) on apples and pears, such as, for example, *V. inaequalis* on apple.

They are particularly suitable for controlling harmful fungi from the class of the Peronosporomycetes (syn. Oomycetes), such as *Peronospora* species, *Phytophthora* species, *Plasmopara viticola*, *Pseudoperonospora* species and *Pythium* species.

The compounds I are also suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces cerevisae*.

The compounds I are employed by treating the fungi or the plants, seeds or materials to be protected against fungal attack or the soil with a fungicidally effective amount of the active compounds. Application can be both before and after the infection of the materials, plants or seeds by the fungi.

The fungicidal compositions generally comprise between 0.1 and 95% by weight, preferably between 0.5 and 90% by weight, of active compound.

When employed in crop protection, the application rates are, depending on the kind of effect desired, between 0.01 and 2.0 kg of active compound per ha.

In seed treatment, the amounts of active compound required are generally from 1 to 1000 g/100 kg of seed, preferably from 5 to 100 g/100 kg of seed.

When used in the protection of materials or stored products, the active compound application rates depend on the kind of application area and on the desired effect. Amounts typically applied in the protection of materials are, for example, from 0.001 g to 2 kg, preferably from 0.005 g to 1 kg, of active compound per cubic meter of treated material.

The compounds of the formula I can be present in different crystal modifications which may differ in their biological activity. They are likewise subject matter of the present invention.

The compounds I can be converted into the customary formulations, for example solutions, emulsions, suspensions, dusts, powders, pastes and granules. The application form depends on the particular purpose; in each case, it should ensure a fine and uniform distribution of the compound according to the invention.

The formulations are prepared in a known manner, for example by extending the active compound with solvents and/or carriers, if desired using emulsifiers and dispersants. Solvents/auxiliaries suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example finely divided silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable for use as surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

The following are examples of formulations: 1. Products for dilution with water

A Water-Soluble Concentrates (SL, LS)

10 parts by weight of the active compounds are dissolved with 90 parts by weight of water or with a water-soluble solvent. As an alternative, wetters or other auxiliaries are added. The active compound dissolves upon dilution with water. This gives a formulation having an active compound content of 10% by weight.

B Dispersible Concentrates (DC)

20 parts by weight of the active compounds are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates (EC)

15 parts by weight of the active compounds are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D Emulsions (EW, EO, ES)

25 parts by weight of the active compounds are dissolved in 35 parts by weight of xylene with addition of calcium dodecylbenzenesulfonate and castor oil ethoxylate (in each case 5 parts by weight). This mixture is added to 30 parts by weight of water by means of an emulsifying machine (e.g. Ultraturrax) and made into a homogeneous emulsion. Dilution with water gives an emulsion. The formulation has an active compound content of 25% by weight.

E Suspensions (SC, OD, FS)

In an agitated ball mill, 20 parts by weight of the active compounds are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules (WG, SG)

50 parts by weight of the active compounds are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders (WP, SP, SS, WS)

75 parts by weight of the active compounds are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations (GF)

20 parts by weight of the active compounds, 10 parts by weight of dispersant, 1 part by weight of gelling agent and 70 parts by weight of water or an organic solvent are ground in a ball mill to give a fine suspension. Dilution with water gives a stable suspension with an active compound content of 20% by weight.

2. Products to be Applied Undiluted

I Dusts (DP, DS)

5 parts by weight of the active compounds are ground finely and mixed intimately with 95 parts by weight of finely divided kaolin. This gives a dustable product with an active compound content of 5% by weight.

J Granules (GR, FG, GG, MG)

0.5 part by weight of the active compounds is ground finely and associated with 99.5 parts by weight of carriers. Current methods are extrusion, spray-drying or the fluidized bed. This gives granules with an active compound content of 0.5% by weight to be applied undiluted.

K ULV Solutions (UL)

10 parts by weight of the active compounds are dissolved in 90 parts by weight of an organic solvent, for example xylene. This gives a product with an active compound content of 10% by weight to be applied undiluted.

Water-soluble concentrates (LS), suspensions (FS), dusts (DS), water-dispersible and water-soluble powders (WS, SS), emulsions (ES), emulsifiable concentrates (EC) and gel formulations (GF) are usually used for the treatment of seed. These formulations can be applied to the seed in undiluted or, preferably, diluted form. The application can be carried out before sowing.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; the intention is to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), by which it is possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate not until immediately prior to use (tank mix). These compositions can be admixed with the compositions according to the invention in a weight ratio of from 1:100 to 100:1, preferably from 1:10 to 10:1.

The following are particularly suitable as adjuvants in this context: organically modified polysiloxanes, for example Break Thru S 240®; alcohol alkoxylates, for example Atplus 245®, Atplus MBA 1303®, Plurafac LF 300® and Lutensol ON 30®; EO-PO block polymers, for example Pluronic RPE 2035® and Genapol B®; alcohol ethoxylates, for example Lutensol XP 80®; and sodium dioctylsulfosuccinate, for example Leophen RA®.

The compositions according to the invention in the application form as fungicides can also be present together with other active compounds, for example with herbicides, insecticides, growth regulators, fungicides or else with fertilizers. When mixing the compounds I or the compositions comprising them with one or more further active compounds, in particular fungicides, it is in many cases possible, for example, to widen the activity spectrum or to prevent the development of resistance. In many cases, synergistic effects are obtained.

The present invention furthermore provides a combination of at least one azolylmethyloxirane of the formula I, in particular an azolylmethyloxirane disclosed in the present description as being preferred, and/or an agriculturally acceptable salt thereof and at least one further fungicidal, insecticidal, herbicidal and/or growth-regulating active compound, it being possible for a synergistic effect to occur.

The present invention also provides a pesticidal composition which comprises at least one compound of the formula I, in particular a compound of the formula I described in the present description as being preferred, and/or an agriculturally acceptable acid addition salt or metal salt thereof and at least one solid or liquid carrier. Such a pesticidal composition may comprise at least one further fungicidally, insecticidally and/or herbicidally active compound, it also being possible for a synergistic effect to occur.

The following list L of fungicides with which the compounds according to the invention can be applied together is meant to illustrate the possible combinations, but not to limit them:

List L:

Strobilurins azoxystrobin, dimoxystrobin, enestroburin, fluoxastrobin, kresoxim-methyl, methominostrobin, orysastrobin, picoxystrobin, pyraclostrobin, pyribencarb, trifloxystrobin, 2-(2-(6-(3-chloro-2-methylphenoxy)-5-fluoropyrimidin-4-yloxy)phenyl)-2-methoxyimino-N-methylacetamide, methyl 2-(ortho-((2,5-dimethylphenyloxymethylene)phenyl)-3-methoxyacrylate, methyl 3-methoxy-2-(2-(N-(4-methoxyphenyl)cyclopropanecarboximidoylsulfanylmethyl)phenyl)acrylate;

Carboxamides carboxanilides: benalaxyl, benalaxyl-M, benodanil, bixafen, boscalid, carboxin, fenfuram, fenhexamid, flutolanil, furametpyr, isotianil, kiralaxyl, mepronil, metalaxyl, ofurace, oxadixyl, oxycarboxin, penthiopyrad, tecloftalam, thifluzamide, tiadinil, 2-amino-4-methylthiazole-5-carboxanilide, 2-chloro-N-(1,1,3-trimethylindan-4-yl)-nicotinamide, N-(3',4'-dichloro-5-fluorobiphenyl-2-yl)-3-difluoromethyl-1-methyl-1H-pyrazole-4-carboxamide, N-[2-(1,3-dimethylbutyl)phenyl]-5-fluoro-1,3-dimethyl-1H-pyrazole-4-carboxamide, N-(4'-chloro-3',5-difluorobiphenyl-2-yl)-3-difluoromethyl-1-methyl-1H-pyrazole-4-carboxamide, N-(4'-chloro-3',5-difluorobiphenyl-2-yl)-3-trifluoromethyl-1-methyl-1H-pyrazole-4-carboxamide, N-(3',4'-dichloro-5-fluorobiphenyl-2-yl)-3-trifluoromethyl-1-methyl-1H-pyrazole-4-carboxamide, N-(3',5-difluoro-4'-methylbiphenyl-2-yl)-3-difluoromethyl-1-methyl-1H-pyrazole-4-carboxamide, N-(3',5-difluoro-4'-methylbiphenyl-2-yl)-3-trifluoromethyl-1-methyl-1H-pyrazole-4-carboxamide, N-(2-bicyclopropyl-2-ylphenyl)-3-difluoromethyl-1-methyl-1H-pyrazole-4-carboxamide, N-(cis-2-bicyclopropyl-2-ylphenyl)-3-difluoromethyl-1-methyl-1H-pyrazole-4-carboxamide, N-(trans-2-bicyclopropyl-2-ylphenyl)-3-difluoromethyl-1-methyl-1H-pyrazole-4-carboxamide, carboxylic acid morpholides: dimethomorph, flumorph;

benzamides: flumetover, fluopicolide, fluopyram, zoxamide, N-(3-ethyl-3,5,5-trimethylcyclohexyl)-3-formylamino-2-hydroxybenzamide;

other carboxamides: carpropamid, diclocymet, mandipropamid, oxytetracyclin, silthiofam, N-(6-methoxypyridin-3-yl)cyclopropanecarboxamide;

Azoles triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chlorophenyl)-2-([1,2,4]triazol-1-yl)-cycloheptanol;

imidazoles: cyazofamid, imazalil, imazalil sulfate, pefurazoate, prochloraz, triflumizole;

benzimidazoles: benomyl, carbendazim, fuberidazole, thiabendazole;

others: ethaboxam, etridiazole, hymexazole, 1-(4-chlorophenyl)-1-(propyn-2-yloxy)-3-(4-(3,4-dimethoxyphenyl)isoxazol-5-yl)propan-2-one;

Nitrogenous Heterocyclyl Compounds pyridines: fluazinam, pyrifenox, 3-[5-(4-chlorophenyl)-2,3-dimethylisoxazolidin-3-yl]-pyridine, 2,3,5,6-tetrachloro-4-methanesulfonylpyridine, 3,4,5-trichloropyridine-2,6-dicarbonitrile, N-(1-(5-bromo-3-chloropyridin-2-yl)ethyl)-2,4-dichloronicotinamide, N-((5-bromo-3-chloropyridin-2-yl)methyl)-2,4-dichloronicotinamide;

pyrimidines: bupirimate, cyprodinil, diflumetorim, fenarimol, ferimzone, mepanipyrim, nitrapyrin, nuarimol, pyrimethanil;

pyrroles: fludioxonil, fenpiclonil;

morpholines: aldimorph, dodemorph, dodemorph acetate, fenpropimorph, tridemorph;

dicarboximides: fluoroimide, iprodione, procymidone, vinclozolin;

others: acibenzolar-5-methyl, amisulbrom, anilazine, blasticidin-S, captafol, captan, quinomethionate, dazomet, debacarb, diclomezine, difenzoquat, difenzoquat methylsulfate, famoxadone, fenamidone, fenoxanil, fenpropidin, folpet, octhilinone, oxolinic acid, piperalin, probenazole, proquinazid, pyroquilon, quinoxyfen, triazoxide, tricyclazole, triforine, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one; carbamates and dithiocarbamates thio- and dithiocarbamates: ferbam, mancozeb, maneb, metam, methasulfocarb, metiram, propineb, thiram, zineb, ziram;

carbamates: diethofencarb, benthiavalicarb, iprovalicarb, propamocarb, propamocarb hydrochloride, valiphenal, 4-fluorophenyl N-(1-(1-(4-cyanophenyl)-ethanesulfonyl)but-2-yl)carbamate;

Other Fungicides guanidines: dodine, dodine free base, guazatine, guazatine acetate, iminoctadine, iminoctadine-triacetate, iminoctadine tris(albesilate);

antibiotics: kasugamycin, kasugamycin hydrochloride hydrate, polyoxins, streptomycin, validamycin A;

nitrophenyl derivatives:

binapacryl, dicloran, dinobuton, dinocap, nitrothal-isopropyl, tecnazen;

organometallic compounds: fentin salts such as, for example, fentin acetate, fentin chloride, fentin hydroxide;

sulfur-containing heterocyclyl compounds: isoprothiolane, dithianon;

organophosphorus compounds: edifenphos, fosetyl, fosetyl aluminum, iprobenfos, pyrazophos, tolclofos methyl;

organochlorine compounds: chlorothalonil, dichlofluanid, dichlorophen, flusulfamide, hexachlorobenzene, pencycuron, pentachlorophenol and salts thereof, phthalide, quintozene, thiophanate methyl, tolylfluanid, N-(4-chloro-2-nitrophenyl)-N-ethyl-4-methylbenzenesulfonamide;

inorganic active compounds: phosphorous acid and salts thereof, sulfur, Bordeaux mixture, copper salts such as, for example, copper acetate, copper hydroxide, copper oxychloride, basic copper sulfate;

others: biphenyl, bronopol, cyflufenamid, cymoxanil, diphenylamine, metrafenone, mildiomycin, oxine-copper, prohexadione-calcium, spiroxamine, tolylfluanid, N-(cyclopropylmethoxyimino-(6-difluoromethoxy-2,3-difluorophenyl)methyl)-2-phenyl acetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)phenyl)-N-ethyl-N-methylformamidine.

The present invention further relates, accordingly, to the compositions that are listed in table B, each line of table B corresponding to a fungicidal composition comprising a compound of the formula I (component 1), which is preferably one of the compounds described herein as being preferred, and comprising the further active compound indicated in each case in the line in question (component 2). According to one embodiment of the invention, component 1 in each line of table B is in each case one of the compounds of the formula I that are specifically individualized in tables 1 to 54.

TABLE B

| Line | Component 1 | Component 2 |
|---|---|---|
| B-1 | a compound of the formula I | azoxystrobin |
| B-2 | a compound of the formula I | dimoxystrobin |
| B-3 | a compound of the formula I | enestroburin |
| B-4 | a compound of the formula I | fluoxastrobin |
| B-5 | a compound of the formula I | kresoxim-methyl |
| B-6 | a compound of the formula I | metominostrobin |
| B-7 | a compound of the formula I | orysastrobin |
| B-8 | a compound of the formula I | picoxystrobin |
| B-9 | a compound of the formula I | pyraclostrobin |
| B-10 | a compound of the formula I | pyribencarb |
| B-11 | a compound of the formula I | trifloxystrobin |
| B-12 | a compound of the formula I | 2-(2-(6-(3-chloro-2-methylphenoxy)-5-fluoropyrimidin-4-yloxy)phenyl)-2-methoxyimino-N-methylacetamide |
| B-13 | a compound of the formula I | methyl 2-(ortho-((2,5-dimethylphenyloxy-methylene)phenyl)-3-methoxyacrylate |
| B-14 | a compound of the formula I | methyl 3-methoxy-2-(2-(N-(4-methoxyphenyl)-cyclopropanecarboximidoylsulfanyl-methyl)phenyl)acrylate |
| B-15 | a compound of the formula I | benalaxyl |
| B-16 | a compound of the formula I | benalaxyl-M |
| B-17 | a compound of the formula I | benodanil |
| B-18 | a compound of the formula I | bixafen |
| B-19 | a compound of the formula I | boscalid |
| B-20 | a compound of the formula I | carboxin |
| B-21 | a compound of the formula I | fenfuram |
| B-22 | a compound of the formula I | fenhexamid |
| B-23 | a compound of the formula I | flutolanil |
| B-24 | a compound of the formula I | furametpyr |
| B-25 | a compound of the formula I | isotianil |
| B-26 | a compound of the formula I | kiralaxyl |
| B-27 | a compound of the formula I | mepronil |
| B-28 | a compound of the formula I | metalaxyl |
| B-29 | a compound of the formula I | ofurace |
| B-30 | a compound of the formula I | oxadixyl |
| B-31 | a compound of the formula I | oxycarboxin |
| B-32 | a compound of the formula I | penthiopyrad |
| B-33 | a compound of the formula I | thifluzamide |
| B-34 | a compound of the formula I | tecloftalam |
| B-35 | a compound of the formula I | tiadinil |
| B-36 | a compound of the formula I | 2-amino-4-methylthiazole-5-carboxanilide |
| B-37 | a compound of the formula I | 2-chloro-N-(1,1,3-trimethylindan-4-yl)-nicotinamide |
| B-38 | a compound of the formula I | N-(3',4'-dichloro-5-fluorobiphenyl-2-yl)-3-difluoromethyl-1-methyl-1H-pyrazole-4-carboxamide |
| B-39 | a compound of the formula I | 5-fluoro-1,3-dimethyl-1H-pyrazole-4-carboxylic acid [2-(1,3-dimethylbutyl)-phenyl]amide |
| B-40 | a compound of the formula I | N-(4'-chloro-3',5-difluorobiphenyl-2-yl)-3-difluoromethyl-1-methyl-1H-pyrazole-4-carboxamide |
| B-41 | a compound of the formula I | N-(4'-chloro-3',5-difluorobiphenyl-2-yl)-3-trifluoromethyl-1-methyl-1H-pyrazole-4-carboxamide |
| B-42 | a compound of the formula I | N-(3',4'-dichloro-5-fluorobiphenyl-2-yl)-3-trifluoromethyl-1-methyl-1H-pyrazole-4-carboxamide |
| B-43 | a compound of the formula I | N-(3',5-difluoro-4'-methylbiphenyl-2-yl)-3-difluoromethyl-1-methyl-1H-pyrazole-4-carboxamide |
| B-44 | a compound of the formula I | N-(3',5-difluoro-4'-methylbiphenyl-2-yl)-3-trifluoromethyl-1-methyl-1H-pyrazole-4-carboxamide |
| B-45 | a compound of the formula I | N-(2-bicyclopropyl-2-yl-phenyl)-3-difluoro-methyl-1-methyl-1H-pyrazole-4-carboxamide |
| B-46 | a compound of the formula I | N-(cis-2-bicyclopropyl-2-yl-phenyl)-3-difluoromethyl-1-methyl-1H-pyrazole-4-carboxamide |
| B-47 | a compound of the formula I | N-(trans-2-bicyclopropyl-2-yl-phenyl)-3-difluoromethyl-1-methyl-1H-pyrazole-4-carboxamide |
| B-48 | a compound of the formula I | dimethomorph |
| B-49 | a compound of the formula I | flumorph |
| B-50 | a compound of the formula I | flumetover |
| B-51 | a compound of the formula I | fluopicolide (picobenzamid) |
| B-52 | a compound of the formula I | fluopyram |
| B-53 | a compound of the formula I | zoxamide |

TABLE B-continued

| Line | Component 1 | Component 2 |
|---|---|---|
| B-54 | a compound of the formula I | N-(3-ethyl-3,5,5-trimethylcyclohexyl)-3-formylamino-2-hydroxybenzamide |
| B-55 | a compound of the formula I | carpropamid |
| B-56 | a compound of the formula I | diclocymet |
| B-57 | a compound of the formula I | mandipropamid |
| B-58 | a compound of the formula I | oxytetracyclin |
| B-59 | a compound of the formula I | silthiofam |
| B-60 | a compound of the formula I | N-(6-methoxypyridin-3-yl)cyclopropane-carboxamide |
| B-61 | a compound of the formula I | azaconazole |
| B-62 | a compound of the formula I | bitertanol |
| B-63 | a compound of the formula I | bromuconazole |
| B-64 | a compound of the formula I | cyproconazole |
| B-65 | a compound of the formula I | difenoconazole |
| B-66 | a compound of the formula I | diniconazole |
| B-67 | a compound of the formula I | diniconazole-M |
| B-68 | a compound of the formula I | enilconazole |
| B-69 | a compound of the formula I | epoxiconazole |
| B-70 | a compound of the formula I | fenbuconazole |
| B-71 | a compound of the formula I | flusilazole |
| B-72 | a compound of the formula I | fluquinconazole |
| B-73 | a compound of the formula I | flutriafol |
| B-74 | a compound of the formula I | hexaconazole |
| B-75 | a compound of the formula I | imibenconazole |
| B-76 | a compound of the formula I | ipconazole |
| B-77 | a compound of the formula I | metconazole |
| B-78 | a compound of the formula I | myclobutanil |
| B-79 | a compound of the formula I | oxpoconazole |
| B-80 | a compound of the formula I | paclobutrazole |
| B-81 | a compound of the formula I | penconazole |
| B-82 | a compound of the formula I | propiconazole |
| B-83 | a compound of the formula I | prothioconazole |
| B-84 | a compound of the formula I | simeconazole |
| B-85 | a compound of the formula I | tebuconazole |
| B-86 | a compound of the formula I | tetraconazole |
| B-87 | a compound of the formula I | triadimenol |
| B-88 | a compound of the formula I | triadimefon |
| B-89 | a compound of the formula I | triticonazole |
| B-90 | a compound of the formula I | uniconazole |
| B-91 | a compound of the formula I | 1-(4-chlorophenyl)-2-([1,2,4]triazol-1-yl)-cycloheptanol |
| B-92 | a compound of the formula I | cyazofamid |
| B-93 | a compound of the formula I | imazalil |
| B-94 | a compound of the formula I | imazalil sulfate |
| B-95 | a compound of the formula I | pefurazoate |
| B-96 | a compound of the formula I | prochloraz |
| B-97 | a compound of the formula I | triflumizole |
| B-98 | a compound of the formula I | benomyl |
| B-99 | a compound of the formula I | carbendazim |
| B-100 | a compound of the formula I | fuberidazole |
| B-101 | a compound of the formula I | thiabendazole |
| B-102 | a compound of the formula I | ethaboxam |
| B-103 | a compound of the formula I | etridiazole |
| B-104 | a compound of the formula I | hymexazole |
| B-105 | a compound of the formula I | fluazinam |
| B-106 | a compound of the formula I | pyrifenox |
| B-107 | a compound of the formula I | 1-(4-chlorophenyl)-1-(propyn-2-yloxy)-3-(4-(3,4-dimethoxyphenyl)isoxazol-5-yl)-propan-2-one |
| B-108 | a compound of the formula I | 3-[5-(4-chlorophenyl)-2,3-dimethyl-isoxazolidin-3-yl]pyridine |
| B-109 | a compound of the formula I | 2,3,5,6-tetrachloro-4-methanesulfonyl-pyridine |
| B-110 | a compound of the formula I | 3,4,5-trichloropyridine-2,6-dicarbonitrile |
| B-111 | a compound of the formula I | N-(1-(5-bromo-3-chloropyridin-2-yl)ethyl)-2,4-dichloronicotinamide |
| B-112 | a compound of the formula I | N-((5-bromo-3-chloropyridin-2-yl)methyl)-2,4-dichloronicotinamide |
| B-113 | a compound of the formula I | bupirimate |
| B-114 | a compound of the formula I | cyprodinil |
| B-115 | a compound of the formula I | diflumetorim |
| B-116 | a compound of the formula I | ferimzone |
| B-117 | a compound of the formula I | fenarimol |
| B-118 | a compound of the formula I | mepanipyrim |
| B-119 | a compound of the formula I | nitrapyrin |
| B-120 | a compound of the formula I | nuarimol |
| B-121 | a compound of the formula I | pyrimethanil |
| B-122 | a compound of the formula I | fludioxonil |

TABLE B-continued

| Line | Component 1 | Component 2 |
|---|---|---|
| B-123 | a compound of the formula I | fenpiclonil |
| B-124 | a compound of the formula I | aldimorph |
| B-125 | a compound of the formula I | dodemorph |
| B-126 | a compound of the formula I | dodemorph acetate |
| B-127 | a compound of the formula I | fenpropimorph |
| B-128 | a compound of the formula I | tridemorph |
| B-129 | a compound of the formula I | fluoroimide |
| B-130 | a compound of the formula I | iprodione |
| B-131 | a compound of the formula I | procymidone |
| B-132 | a compound of the formula I | vinclozolin |
| B-133 | a compound of the formula I | acibenzolar-S-methyl |
| B-134 | a compound of the formula I | amisulbrom |
| B-135 | a compound of the formula I | anilazine |
| B-136 | a compound of the formula I | blasticidin-S |
| B-137 | a compound of the formula I | captan |
| B-138 | a compound of the formula I | captafol |
| B-139 | a compound of the formula I | chinomethionat |
| B-140 | a compound of the formula I | dazomet |
| B-141 | a compound of the formula I | debacarb |
| B-142 | a compound of the formula I | diclomezine |
| B-143 | a compound of the formula I | difenzoquat |
| B-144 | a compound of the formula I | difenzoquat methylsulfate |
| B-145 | a compound of the formula I | famoxadone |
| B-146 | a compound of the formula I | fenamidone |
| B-147 | a compound of the formula I | fenoxanil |
| B-148 | a compound of the formula I | fenpropidin |
| B-149 | a compound of the formula I | folpet |
| B-150 | a compound of the formula I | octhilinone |
| B-151 | a compound of the formula I | oxolinic acid |
| B-152 | a compound of the formula I | piperalin |
| B-153 | a compound of the formula I | probenazole |
| B-154 | a compound of the formula I | proquinazid |
| B-155 | a compound of the formula I | pyroquilon |
| B-156 | a compound of the formula I | quinoxyfen |
| B-157 | a compound of the formula I | triazoxide |
| B-158 | a compound of the formula I | tricyclazole |
| B-159 | a compound of the formula I | triforine |
| B-160 | a compound of the formula I | 5-chloro-7-(4-methylpiperidin-1-yl)-6-(2,4,6-trifluorophenyl)-[1,2,4]triazolo-[1,5-a]pyrimidine |
| B-161 | a compound of the formula I | 2-butoxy-6-iodo-3-propylchromen-4-one |
| B-162 | a compound of the formula I | ferbam |
| B-163 | a compound of the formula I | mancozeb |
| B-164 | a compound of the formula I | maneb |
| B-165 | a compound of the formula I | metiram |
| B-166 | a compound of the formula I | metam |
| B-167 | a compound of the formula I | methasulfocarb |
| B-168 | a compound of the formula I | propineb |
| B-169 | a compound of the formula I | thiram |
| B-170 | a compound of the formula I | zineb |
| B-171 | a compound of the formula I | ziram |
| B-172 | a compound of the formula I | diethofencarb |
| B-173 | a compound of the formula I | flubenthiavalicarb |
| B-174 | a compound of the formula I | iprovalicarb |
| B-175 | a compound of the formula I | propamocarb |
| B-176 | a compound of the formula I | propamocarb hydrochloride |
| B-177 | a compound of the formula I | methyl 3-(4-chlorophenyl)-3-(2-isopropoxy-carbonylamino-3-methylbutyrylamino)-propionate |
| B-178 | a compound of the formula I | valiphenal |
| B-179 | a compound of the formula I | 4-fluorophenyl N-(1-(1-(4-cyanophenyl)-ethanesulfonyl)but-2-yl)carbamate |
| B-180 | a compound of the formula I | dodine |
| B-181 | a compound of the formula I | dodine free base |
| B-182 | a compound of the formula I | iminoctadine |
| B-183 | a compound of the formula I | iminoctadine triacetate |
| B-184 | a compound of the formula I | iminoctadine tris(albesilate) |
| B-185 | a compound of the formula I | guazatine |
| B-186 | a compound of the formula I | guazatine acetate |
| B-187 | a compound of the formula I | kasugamycin |
| B-188 | a compound of the formula I | kasugamycin hydrochloride hydrate |
| B-189 | a compound of the formula I | polyoxine |
| B-190 | a compound of the formula I | streptomycin |
| B-191 | a compound of the formula I | validamycin A |
| B-192 | a compound of the formula I | binapacryl |
| B-193 | a compound of the formula I | dicloran |
| B-194 | a compound of the formula I | dinobuton |
| B-195 | a compound of the formula I | dinocap |

TABLE B-continued

| Line | Component 1 | Component 2 |
|---|---|---|
| B-196 | a compound of the formula I | nitrothal-isopropyl |
| B-197 | a compound of the formula I | tecnazen |
| B-198 | a compound of the formula I | fentin acetate |
| B-199 | a compound of the formula I | fentin chloride |
| B-200 | a compound of the formula I | fentin hydroxide |
| B-201 | a compound of the formula I | isoprothiolane |
| B-202 | a compound of the formula I | dithianon |
| B-203 | a compound of the formula I | edifenphos |
| B-204 | a compound of the formula I | fosetyl |
| B-205 | a compound of the formula I | fosetyl aluminum |
| B-206 | a compound of the formula I | iprobenfos |
| B-207 | a compound of the formula I | pyrazophos |
| B-208 | a compound of the formula I | tolclofos-methyl |
| B-209 | a compound of the formula I | chlorothalonil |
| B-210 | a compound of the formula I | dichlofluanid |
| B-211 | a compound of the formula I | dichlorophen |
| B-212 | a compound of the formula I | flusulfamide |
| B-213 | a compound of the formula I | hexachlorobenzene |
| B-214 | a compound of the formula I | pencycuron |
| B-215 | a compound of the formula I | pentachlorophenol and salts thereof |
| B-216 | a compound of the formula I | phthalide |
| B-217 | a compound of the formula I | quintozene |
| B-218 | a compound of the formula I | thiophanate methyl |
| B-219 | a compound of the formula I | tolylfluanid |
| B-220 | a compound of the formula I | N-(4-chloro-2-nitrophenyl)-N-ethyl-4-methylbenzenesulfonamide |
| B-221 | a compound of the formula I | phosphorous acid and salts thereof |
| B-222 | a compound of the formula I | sulfur |
| B-223 | a compound of the formula I | Bordeaux mixture |
| B-224 | a compound of the formula I | copper acetate |
| B-225 | a compound of the formula I | copper hydroxide |
| B-226 | a compound of the formula I | copper oxychloride |
| B-227 | a compound of the formula I | basic copper sulfate |
| B-228 | a compound of the formula I | biphenyl |
| B-229 | a compound of the formula I | bronopol |
| B-230 | a compound of the formula I | cyflufenamid |
| B-231 | a compound of the formula I | cymoxanil |
| B-232 | a compound of the formula I | diphenylamine |
| B-233 | a compound of the formula I | metrafenone |
| B-234 | a compound of the formula I | mildiomycin |
| B-235 | a compound of the formula I | oxine-copper |
| B-236 | a compound of the formula I | prohexadione-calcium |
| B-237 | a compound of the formula I | spiroxamine |
| B-238 | a compound of the formula I | tolylfluanid |
| B-239 | a compound of the formula I | N-(cyclopropylmethoxyimino-(6-difluoro-methoxy-2,3-difluorophenyl)-methyl)-2-phenylacetamide |
| B-240 | a compound of the formula I | N'-(4-(4-chloro-3-trifluoromethylphenoxy)-2,5-dimethylphenyl)-N-ethyl-N-methyl-formamidine |
| B-241 | a compound of the formula I | N'-(4-(4-fluoro-3-trifluoromethylphenoxy)-2,5-dimethylphenyl)-N-ethyl-N-methyl-formamidine |
| B-242 | a compound of the formula I | N'-(2-methyl-5-trifluoromethyl-4-(3-tri-methylsilanylpropoxy)phenyl)-N-ethyl-N-methylformamidine |
| B-243 | a compound of the formula I | N'-(5-difluoromethyl-2-methyl-4-(3-tri-methylsilanylpropoxy)phenyl)-N-ethyl-N-methylformamidine |

The active compounds II specified above as component 2, their preparation, and their effect against fungal pathogens are widely known; they are available commercially. The compounds with IUPAC nomenclature, their preparation, and their fungicidal activity are likewise known [cf. EP-A 226 917; EP-A 10 28 125; EP-A 10 35 122; EP-A 12 01 648; WO 98/46608; WO 99/24413; WO 03/14103; WO 03/053145; WO 03/066609; WO 04/049804].

SYNTHESIS EXAMPLES

Prepared was the active compound 1-[3-(2,2-difluorobenzo[1,3]dioxol-5-yl)-2-(4-fluoro-phenyl)oxiranylmethyl]-1H-[1,2,4]triazole having the following physical properties:

H-NMR (CDCl3, 300 MHz): 7.78-7.82 (2H), 7.32-7.00 (7H), 4.68 (1H), 4.18-4.13 (2H).

The invention claimed is:

1. A compound of formula I

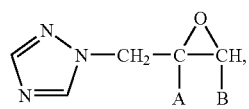

(I)

wherein

A or B is benzodioxolyl which is substituted by one to five of the following substituents: halogen, CN, NO$_2$, amino, C$_1$-C$_4$-alkyl, C$_1$-C$_4$-alkoxy, C$_1$-C$_4$-haloalkyl, C$_1$-C$_4$-haloalkoxy, C$_1$-C$_4$-alkylamino, C$_1$-C$_4$-dialkylamino, thio or C$_1$-C$_4$-alkylthio, and the respective other substituent A or B is phenyl or 5-membered or 6-membered heteroaryl, these substituents optionally being substituted by one to three of the following substituents: halogen, CN, NO$_2$, amino, C$_1$-C$_4$-alkyl, C$_1$-C$_4$-alkoxy, C$_1$-C$_4$-haloalkyl, C$_1$-C$_4$-haloalkoxy, C$_1$-C$_4$-alkylamino, C$_1$-C$_4$-dialkylamino, thio or C$_1$-C$_4$-alkylthio, or a plant-compatible acid addition salt or metal salt thereof.

2. The compound of claim 1, wherein said benzodioxolyl is substituted by one to five of the following substituents: halogen, C$_1$-C$_4$-alkyl, C$_1$-C$_4$-alkoxy, C$_1$-C$_4$-haloalkyl or C$_1$-C$_4$-haloalkoxy.

3. The compound of claim 2, wherein said benzodioxolyl is substituted by one to five of the following substituents: halogen, C$_1$-C$_4$-alkyl or C$_1$-C$_4$-alkoxy.

4. The compound of claim 2, wherein said benzodioxolyl is substituted by two halogen in the dioxolyl ring.

5. The compound of claim 4, wherein said benzodioxolyl is substituted by one to five halogen.

6. The compound of claim 1, wherein said phenyl is substituted by one to three of the following substituents: halogen, CN, NO$_2$, amino, C$_1$-C$_4$-alkyl, C$_1$-C$_4$-alkoxy, C$_1$-C$_4$-haloalkyl, C$_1$-C$_4$-haloalkoxy, C$_1$-C$_4$-alkylamino, C$_1$-C$_4$-dialkylamino, thio or C$_1$-C$_4$-alkylthio.

7. The compound of claim 1, wherein said phenyl is substituted by one to three of the following substituents: halogen, C$_1$-C$_4$-alkyl, C$_1$-C$_4$-alkoxy, C$_1$-C$_4$-haloalkyl or C$_1$-C$_4$-haloalkoxy.

8. The compound of claim 1, wherein said phenyl is substituted by one to three of the following substituents: halogen, C$_1$-C$_4$-alkyl or C$_1$-C$_4$-alkoxy.

9. The compound of claim 1, wherein said 5-membered heteroaryl is selected from the group consisting of furyl, thienyl, pyrrolyl, pyrazolyl, imidazolyl, triazolyl, tetrazolyl, oxazolyl, isoxazolyl, 1,3,4-oxadiazolyl, thiazolyl, isothiazolyl and thiadiazolyl.

10. The compound of claim 9, wherein said 5-membered heteroaryl is selected from the group consisting of furyl, thienyl, pyrrolyl, pyrazolyl, triazolyl and thiazolyl.

11. The compound of claim 10, wherein said 5-membered heteroaryl is selected from the group consisting of thienyl, triazolyl and pyrazolyl.

12. The compound of claim 1, wherein said 6-membered heteroaryl is selected from the group consisting of pyridinyl, pyrimidinyl, pyrazinyl, pyridazinyl, 1,2,3-triazinyl, 1,2,4-triazinyl and 1,3,5-triazinyl.

13. The compound of claim 12, wherein said 6-membered heteroaryl is selected from the group consisting of pyridyl and pyrimidinyl.

14. A crop protection composition comprising a solid or liquid carrier and a compound of formula I of claim 1 and/or an acid addition salt or metal salt thereof.

15. Seed comprising at least one compound of formula I of claim 1 and/or an acid addition salt or metal salt thereof.

16. A method for controlling phytopathogenic fungi wherein the fungi or the materials, plants, the soil or seed to be protected against fungal attack are/is treated with an effective amount of a compound of formula I of claim 1 or an acid addition salt or metal salt thereof.

* * * * *